(12) United States Patent
Swinson et al.

(10) Patent No.: US 9,150,480 B2
(45) Date of Patent: Oct. 6, 2015

(54) SYNTHESIS OF FLUORINATED ETHERS

(75) Inventors: Joel Swinson, Evans, GA (US); Barry Jones, Martinez, GA (US); Danny Graham, Martinez, GA (US); Neville Pavri, Evans, GA (US)

(73) Assignee: HALOCARBON PRODUCTS CORPORATION, River Edge, NJ (US)

( * ) Notice: Subject to any disclaimer, the term of this patent is extended or adjusted under 35 U.S.C. 154(b) by 352 days.

(21) Appl. No.: 11/813,785

(22) PCT Filed: Jan. 6, 2006

(86) PCT No.: PCT/US2006/000750
§ 371 (c)(1),
(2), (4) Date: Aug. 31, 2007

(87) PCT Pub. No.: WO2006/076324
PCT Pub. Date: Jul. 20, 2006

(65) Prior Publication Data
US 2008/0132731 A1    Jun. 5, 2008

Related U.S. Application Data

(60) Provisional application No. 60/643,301, filed on Jan. 12, 2005.

(51) Int. Cl.
*C07C 41/22* (2006.01)
*C07C 43/12* (2006.01)

(52) U.S. Cl.
CPC ............... *C07C 43/123* (2013.01); *C07C 41/22* (2013.01)

(58) Field of Classification Search
CPC ............................. C07C 41/22; C07C 43/123
See application file for complete search history.

(56) References Cited

U.S. PATENT DOCUMENTS

| 3,258,500 | A | * | 6/1966 | Swamer et al. ............... 570/169 |
| 3,535,388 | A | | 10/1970 | Terrell |
| 3,535,425 | A | | 10/1970 | Terrell |
| 3,804,778 | A | | 4/1974 | Ramanadin et al. |
| 4,088,701 | A | * | 5/1978 | Siegemund et al. .......... 568/683 |
| 5,026,924 | A | * | 6/1991 | Cicco ........................... 568/683 |
| 6,555,086 | B2 | | 4/2003 | Ewing et al. |
| 6,849,194 | B2 | | 2/2005 | Robin et al. |
| 2003/0209685 | A1 | | 11/2003 | Robin |

* cited by examiner

*Primary Examiner* — Rosalynd Keys
(74) *Attorney, Agent, or Firm* — Norris McLaughlin & Marcus, P.A.

(57) ABSTRACT

A process for preparing fluorinated ethers, such as desflurane, comprises reacting the corresponding chlorinated ether, such as isoflurane, with anhydrous hydrogen fluoride in the vapor phase in the presence of chromia catalyst. It is emphasized that this abstract is provided to comply with the rules requiring an abstract which will allow a searcher or other reader quickly to ascertain the subject matter of the technical disclosure. It is submitted with the understanding that it will not be used to interpret or limit the scope or meaning of the appended issued claims.

16 Claims, No Drawings

SYNTHESIS OF FLUORINATED ETHERS

BACKGROUND OF THE INVENTION

1. Field of the Invention

The present invention relates generally to the preparation of fluorinated ethers, which are useful as inhalation anesthetics.

2. Description of Related Art

Desflurane is a well known compound with effective anesthetic properties. For example see E. I. Eger et al, *Anesthesia and Analgesia*, 1987, pp 971-973, 974-976, 977-982, 983-985, 1227-1229, 1230-1233 and 1312-1315.

This compound is mentioned in U.S. Pat. No. 3,897,502, where it is prepared by the direct fluorination of 2-difluoromethoxy-1,1,1-trifluoroethane in Freon E3 as solvent, using 20% fluorine gas in argon. The reaction took 13 hours and had to be carried out at −20° C. to −25° C. to control the exothermic process. This process would be difficult to scale up due to the slow reaction, low reaction temperature and expensive reagents. Also, it is known to those skilled in the art that special care needs to be taken since the interaction of fluorine gas with partially fluorinated hydrocarbons is liable to cause explosions.

Other methods available for synthesis of desflurane involve:

a) Reaction of $CHCl_2OCH_2COCl$ and/or $CHCl_2OCHClCOCl$ with sulfur tetrafluoride (U.S. Pat. No. 4,855,511). This is a multistage process and involves handling of highly toxic gaseous reagent sulfur tetrafluoride.

b) Reaction of $CF_3CHClOCF_2H$ (isoflurane) with potassium fluoride. This reaction can be carried out in the absence of solvent at 278° C. under a pressure of 500 psi in an autoclave (U.S. Pat. No. 4,874,901) or in presence of an aprotic solvent (like sulfolane) with a phase transfer catalyst (tetramethylammonium chloride) at 210° C. again under pressure (UK Patent Specification No. 2,219,292). These processes have to be operated at high pressure and at elevated temperature for a long period of time and hence suffer from high capital cost. In addition, these processes have a further disadvantage in that they are essentially batch processes.

c) Reaction of $CF_3CHClOCF_2H$ (isoflurane) with bromine trifluoride at ambient temperature (U.S. Pat. No. 5,015,781). Although this process gives a good yield and the transformation is accomplished in a short time, the reagent bromine trifluoride which is prepared from fluorine and bromine, is a highly toxic and hazardous chemical, which can explode in contact with water or organic materials. Special care and engineering are required for safe use which makes handling it on a commercial scale quite difficult. Additionally $BrF_3$ is an expensive fluorinating agent.

d) Reaction of $CF_3CH_2OCF_2H$ with a solid transition metal fluoride fluorinating agent, where the fluorinating agent is $CoF_3$ (U.S. Pat. No. 6,054,626). This process, according to the examples listed therein, gives a low yield (30-40%) of crude desflurane which has to be further purified for use as an anesthetic.

e) Reaction of $CF_3CHClOCF_2H$ (isoflurane) with HF in the presence of antimony pentachloride, alone or in combination with antimony trichloride (U.S. Pat. Nos. 5,026,924 and 6,800,786). This process suffers from several drawbacks, including the use of highly toxic and environmentally troublesome antimony salts which must be removed as an aqueous waste stream. The process also results in the formation of very difficult to separate byproducts, the removal of which results in increased energy consumption, and more significantly, results in a reduced yield of desflurane.

Accordingly, an object of the present invention was to provide a process whereby fluorinated ethers, including desflurane, can be prepared on an industrial scale without significant problems.

BRIEF SUMMARY OF THE INVENTION

This and other objects were met with the present invention. Thus, it has been found that certain aliphatic fluorinated ethers, including desflurane, can be produced from the corresponding chlorinated ethers by contacting the latter with anhydrous hydrogen fluoride in the vapor phase in the presence of a chromia catalyst. The term "chromia catalyst," as used herein, refers to a catalyst comprising chromium having a valence of 3 to 6, wherein the catalyst is selected from the group consisting of chromium oxides, chromium halides, chromium oxides treated with halides, and mixtures thereof.

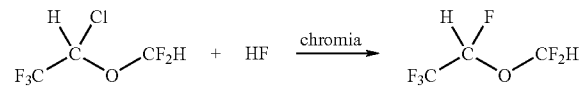

DETAILED DESCRIPTION OF THE INVENTION

The present invention provides a process for the preparation of fluorinated ethers of the formula:

where R is hydrogen, fluorine or an alkyl group, R' is hydrogen, an alkyl group or a fluoroalkyl group and R" is fluorine or a fluoroalkyl group, which process comprises reacting a chlorinated ether of the formula:

(where, R, R' and R" are as hereinbefore defined) with anhydrous HF over chromia catalyst as shown in the above reaction scheme.

In the preferred operation of the process R is hydrogen, R' is hydrogen and R" is fluorine, i.e., the process produces desflurane starting from isoflurane.

Using this new process, $CF_3CHClOCF_2H$ (isoflurane) can be fluorinated under relatively mild conditions in the vapor phase to $CF_3CHFOCF_2H$ (desflurane) using excess anhydrous HF over chromia catalyst. Preferably, the process is continuous and is not limited to a particular pressure, since it may be run at reduced pressure, ambient pressure or at elevated pressure. Almost no by-products are seen, which results in no loss of product due to issues relating to separation of by-products from desflurane, as is the case with examples in the related art.

The chromia catalyst used in the reaction can be prepared by methods known to those skilled in the art, for example, those described in U.S. Pat. No. 6,706,935, the entire contents of which are incorporated herein by reference. Preferably, the chromia catalyst is a chromium oxide, for example, $Cr_2O_3$; or a chromium halide, for example, $CrX_3$, where each X is the same or a different halogen, especially fluorine or chlorine; or a chromium oxide, for example, $Cr_2O_3$, treated with a halide, for example, $CCl_3F$ or $CCl_4$, or a fluorinating agent such as HF. Preferably, the chromia catalyst is prepared by a method that comprises annealing, drying and/or partially fluorinating it using a fluorinating agent such as HF. It can be used in form of pellets, granules or as a powder. The chromia catalyst can be unsupported, but can also be deposited on a solid support such as alumina or may be doped with transition metal ions.

The process of the present invention thus provides a safe and economic route to desflurane which can be easily developed to commercial scale.

The fluorination in general will be carried out by contacting HF and $CF_3CHClOCF_2H$ with chromia catalyst. The HF and $CF_3CHClOCF_2H$ can be liquid and/or vapor phase and the catalyst can be in a packed or simulated moving bed or in a stirred tank reactor.

The starting chlorinated ether has a boiling point of 48.5° C. and can be vaporized easily by heating. In one embodiment the fluorination will be carried out by contacting HF vapor and $CF_3CHClOCF_2H$ vapor over a packed or simulated moving bed of chromia catalyst at temperatures of 80 to 45° C., preferably 100 to 300° C. and most preferably 120-200° C. The reaction can be carried out at elevated pressure, reduced pressure or at atmospheric pressure. While the starting material is preferably introduced as a vapor, it can also be introduced in liquid form. If desired, the starting material can be introduced by mixing with an inert carrier gas.

In a preferred embodiment of the reaction, the starting material $CF_3CHClOCF_2H$ and excess HF are continuously introduced in vapor form over a chromia catalyst bed. The amount of HF used can be between 0.25 to 25 mole equivalents for each mole of $CF_3CHClOCF_2H$, more preferably between 1 to 15 equivalents of HF and most preferably between 2 to 6 equivalents of HF. The HCl, unreacted HF, unreacted $CF_3CHClOCF_2H$ and desflurane are then collected in another vessel or a column where HCl is removed and unreacted HF and $CF_3CHClOCF_2H$ are recycled using fractional distillation.

The separation of product/unreacted starting materials and HCl may be either continuous or batch and is not limited as to pressure, which may be at reduced pressure, ambient pressure or at elevated pressure. In actual practice, it would be preferred to operate at higher pressure to allow for greater fractional distillation efficiency. The separation method used may be fractional distillation, solvent extraction, washing with water and the like.

The following examples illustrate the present invention and should not be construed in any way as limiting its scope.

Example 1

A 1-foot by 1-inch stainless steel tube was filled with chromia catalyst and heated to 175° C. $CF_3CHClOCF_2H$ was fed into the tube using nitrogen as a carrier gas at the rate of 20 ml/min. The amount of $CF_3CHClOCF_2H$ fed was 0.07 moles/hr along with excess HP vapor. After passing over the chromia bed, the material went into a water scrubber to remove HF and HCl. The scrubber was connected to a cold trap. The contents of the cold trap were weighed and analyzed using a GC/MS. The analysis indicated the following: Desflurane 75.30%, $CF_3CHClOCF_2H$ 24.58%, total other by-products 0.12% (R123, R124, R125).

Example 2

A 1-foot by 1-inch stainless steel tube was filled with chromia catalyst and heated to 170° C. In this case, no carrier gas was used. The $CF_3CHClOCF_2H$ was vaporized using a pre-heater before it reached the tube containing chromia. The amount of $CF_3CHClOCF_2H$ fed was 0.23 moles/hr and the amount of HF fed was 2.3 moles/hr. After passing over the chromia bed, the material went into a water scrubber to remove HF and HCl. The scrubber was connected to a cold trap. The contents of the cold trap were weighed and analyzed using a GC/MS. Analysis indicated desflurane 76.02%, $CF_3CHClOCF_2H$ 14.65%, other by-products 9.33% (R123, R124, R125)

Example 3

A 1-foot by 1-inch stainless steel tube was filled with chromia catalyst and heated to 140° C. In this case, no carrier gas was used. The $CF_3CHClOCF_2H$ was vaporized using a pre-heater before it reached the tube containing chromia. The amount of $CF_3CHClOCF_2H$ fed was 0.32 moles/hr and the amount of HF fed was 1.5 moles/hr. After passing over the chromia bed, the material was collected into a cold bomb and the bomb was weighed. A mass balance of 95% was obtained. The contents of the bomb were passed through water to remove HF and HCl and the organic material was collected in a cold trap and analyzed using GC/MS. Analysis indicated 46.14% desflurane, 53.86% isoflurane and <0.1% by-products. This corresponds to a 95% yield of desflurane.

It should be understood that the preceding detailed description of the invention is merely a detailed description of one preferred embodiment or of a small number of preferred embodiments of the present invention and that numerous changes to the disclosed embodiment(s) can be made in accordance with the disclosure herein without departing from the spirit or scope of the invention. The preceding detailed description of the invention, therefore, is not meant to limit the scope of the invention in any respect. Rather, the scope of the invention is to be determined only by the appended issued claims and their equivalents.

What is claimed is:

1. A process for the preparation of 2-difluoromethoxy-1,1,1,2-tetrafluoroethane (desflurane) of the formula:

which comprises reacting 2-chloro-2-difluoromethoxy-1,1,1-trifluoroethane (isoflurane) of the formula:

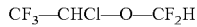

with anhydrous HF in the presence of a chromia catalyst.

2. The process according to claim 1, where the isoflurane and HF are reacted in the vapor phase at a temperature of 80-450° C. over a bed of chromia catalyst.

3. The process according to claim 2, where the isoflurane and HF are reacted in the vapor phase at a temperature of 120-200° C. over a bed of chromia catalyst.

4. The process according to claim 1, where the isoflurane is introduced over chromia catalyst as vapor, liquid or by mixing with an inert carrier gas.

5. The process according to claim 1, which is operated continuously and the isoflurane and HF vapors are fed continuously over chromia catalyst using a 0.25 to 25 molar equivalent of HF.

6. The process according to claim 5, wherein the isoflurane and HF vapors are fed continuously over chromia catalyst using a 1 to 15 molar equivalent of HF.

7. The process according to claim 6, wherein the isoflurane and HF vapors are fed continuously over chromia catalyst using a 2 to 6 molar equivalent of HF.

8. The process according to claim 1, where the reacting is carried out at reduced pressure.

9. The process according to claim 1, where the reacting is carried out at elevated pressure.

10. The process according to claim 1, where the reacting is carried out at atmospheric pressure.

11. The process according to claim 1, which further comprises separating product from unreacted starting materials and HCl in a batchwise or continuous manner and at reduced pressure.

12. The process according to claim 1, which further comprises separating product from unreacted starting materials and HCl in a batchwise or continuous manner and at ambient pressure.

13. The process according to claim 1, which further comprises separating product from unreacted starting materials and HCl in a batchwise or continuous manner and at elevated pressure.

14. The process according to claim 1, which produces less than 10% of byproducts, exclusive of unreacted isoflurane.

15. The process according to claim 1, which produces less than 1% of byproducts, exclusive of unreacted isoflurane.

16. The process according to claim 1, wherein the chromia catalyst is selected from the group consisting of chromium oxide, chromium halide and halide-treated chromium oxide.

* * * * *